United States Patent
Cindric et al.

(10) Patent No.: US 9,581,601 B2
(45) Date of Patent: Feb. 28, 2017

(54) METHOD OF DETECTION OF AMINO ACID SEQUENCE AND/OR IDENTIFICATION OF PEPTIDES AND PROTEINS, BY USE OF A NEW DERIVATIZATION REAGENT AND SYNTHESIS OF 5-FORMYL-BENZENE-1,3-DISULPHONIC ACID AS DERIVATIZATION REAGENT

(75) Inventors: Mario Cindric, Zagreb (HR); Zdenko Hamersak, Zagreb (HR); Ivana Dodig, Zagreb (HR)

(73) Assignee: Rudjer Boskovic Institute, Zagreb (HR)

( * ) Notice: Subject to any disclaimer, the term of this patent is extended or adjusted under 35 U.S.C. 154(b) by 323 days.

(21) Appl. No.: 14/117,395

(22) PCT Filed: May 18, 2011

(86) PCT No.: PCT/HR2011/000019
§ 371 (c)(1),
(2), (4) Date: Nov. 13, 2013

(87) PCT Pub. No.: WO2012/156764
PCT Pub. Date: Nov. 22, 2012

(65) Prior Publication Data
US 2015/0233937 A1    Aug. 20, 2015

(51) Int. Cl.
*G01N 33/68* (2006.01)
*C07C 303/02* (2006.01)
*C07C 303/22* (2006.01)
*C07C 333/04* (2006.01)

(52) U.S. Cl.
CPC ....... *G01N 33/6848* (2013.01); *C07C 303/02* (2013.01); *C07C 303/22* (2013.01); *C07C 333/04* (2013.01)

(58) Field of Classification Search
CPC .... G01N 33/68; C07C 303/02; C07C 303/22; C07C 333/04
See application file for complete search history.

(56) References Cited

U.S. PATENT DOCUMENTS

| 7,338,806 | B2 * | 3/2008 | Chen | G01N 33/6842 436/57 |
| 2007/0128729 | A1 * | 6/2007 | Puente | G01N 33/6842 436/86 |

FOREIGN PATENT DOCUMENTS

WO    WO 0043792 A2 * 7/2000    ............. C07K 1/128

OTHER PUBLICATIONS

Abstract of Cerfontain, Hans et al. "4. The positional reactivity order in the sulfur trioxide sulfonation of benzene and napthalene derivatives containing an electron-withdrawning substituent." Recueil des Travaux Chimiques des Pays-Bas (1994) 113 403-10.*
Friedman, Mendel et al. "Reductive alkylation of proteins with aromatic aldehydes and sodium cyanoborohydride." Int. J. Peptide Protein Res. (1974) 6 183-185.*
Hassell, Kerry M. et al. "Gas-Phase Bioconjugation of Peptides via Ion/Ion Charge Inversion: Schiff Base Formation on the Conversion of Cations to Anions." Anal. Chem. (2010) 82 1594-1597.*
Samyn, Bart et al. "A case study of de novo sequence analysis of N-sulfonated peptides by MALDI TOF/TOF mass spectrometry." Am. Soc. Mass Spec. (2004) 15 1838-1582.*
Gevaert et al., "Protein Identification Methods in Proteomics", Electrophoresis 2000, 21, Proteomics and 2-DE, pp. 1145-1154.
Steen et al., "The ABC'S (and XYZ'S) of Peptide Sequencing", Nature Reviews, Molecular Cell Biology, vol. 5, Sep. 2004, pp. 699-711.
Conrotto et al. "Sulfonation Chemistry as a Powerful Tool for MALDI TOF/TOF de Novo Sequencing and Post-Translational Modification Analysis", Journal of Biomolecular Techniques , vol. 16, Issue 4, Dec. 2005, pp. 441-452.
Keough et al., "Derivatization Procedures to Facilitate de novo Sequencing of Lysine-Terminated Tryptic Peptides using Postsource Decay Matrix-Assisted Laser Desorption/Ionization Mass Spectrometry", Rapid Communications in Mass Spectrometry, 14, 2000, pp. 2348-2356.
Lee et al., "Highly Informative Proteome Analysis by Combining Improved N-Terminal Sulfonation for de novo Peptide Sequencing online Capillary Reverse-Phase Liquid Chromatography/Tandem Mass Spectrometry", Proteomics 2004, vol. 4, pp. 1684-1694.
Corey et al., "Pyridinium Chlorochromate. An Efficient Reagent for Oxidation of Primary and Secondary Alcohols to Carbonyl Compounds", Tetrahedron Letters No. 31, 1975, pp. 2647-2650.
Chen et al. "De novo Sequencing of Tryptic Peptides Sulfonated by 4-Sulfophenyl Isothiocyanate for Unambiguous Protein Identification using Post-source Decay Matrix-Assisted Laser Desorption/Ionization Mass Spectrometry", Rapid Communications in Mass Spectrometry, 2004, vol. 18, pp. 191-198.
Keough et al., "A Method for High-Sensitivity Peptide Sequencing using Postsource Decay Matrix-Assisted Laser Desorption Ionization Mass Spectrometry", Proc. Natl. Acad. Sci., vol. 96, Jun. 1999, Chemistry, pp. 7131-7136.
Alley, Jr., et al., "Improved Collision-Induced Dissociation Analysis of Peptides by Matrix-Assisted Laser Desorption/Ionization Tandem Time-of-Flight Mass Spectrometry through 3-Sulfobenzoic Acid Succinimidyl Ester Labeling", Journal of Proteome Research, 2007, vol. 6, pp. 124-132.

* cited by examiner

*Primary Examiner* — Christopher A Hixson
(74) *Attorney, Agent, or Firm* — Nixon Peabody LLP; Jeffrey L. Costellia

(57) ABSTRACT

Present invention refers to a novel and improved method of derivatization and detection of amino acid sequence and/or identification of proteins, peptides by a new derivatization compound. Precisely, the method discloses a novel approach to derivatization of peptides or proteins by compounds comprising two or more sulfonyl groups and analysis of derivatized analytes in negative mode of operation of mass spectrometer. This method allows unambiguous analysis of amino acid sequence of long-chain peptides/proteins. Also, the invention discloses a novel synthesis procedure of 5-formyl-benzene-1,3-disulphonic acid as derivatization compound.

2 Claims, 3 Drawing Sheets

METHOD OF DETECTION OF AMINO ACID SEQUENCE AND/OR IDENTIFICATION OF PEPTIDES AND PROTEINS, BY USE OF A NEW DERIVATIZATION REAGENT AND SYNTHESIS OF 5-FORMYL-BENZENE-1,3-DISULPHONIC ACID AS DERIVATIZATION REAGENT

SEQUENCE LISTING

The instant application contains a Sequence Listing which has been submitted electronically in ASCII format and is hereby incorporated by reference in its entirety. Said ASCII copy, created on Mar. 31, 2015, is named 045073-20_SL.txt and is 747 bytes in size.

The subject invention refers to a novel and improved method of detection of amino acid sequence and/or identification of proteins, peptides. Precisely, the method discloses a novel approach to peptide or protein derivatization and analysis of resulting analytes in negative mode of operation of mass spectrometer with possibility of amino acid sequencing in positive ion mode. Furthermore, the invention also relates to synthesis of 5-formyl-benzene-1,3-disulphonic acid used as derivatization agent in the foregoing method.

Technical Problem

Protein identification by peptide mass fingerprinting (PMF) using the MS/MS techniques (tandem mass spectrometry) post-source decay (PSD) or collision-induced dissociation (CID) is based on the comparison of experimentally derived data with theoretically calculated peptide masses and fragmentation ions masses in databases (Gevaert et al. Electrophoresis 2001). However, since genome sequence of most organisms is still unraveled, information on particular proteins is not included in existing databases. In addition, even if relevant protein information existed in the databases, different modifications such as post-translational modifications can hamper identification of a portion or a complete amino acid sequence. Therefore, complete determination of primary protein structure requires detection of amino acid sequence with the minimal use of databases, i.e., de novo peptide and protein sequencing (H. Steen et al. Mol. Cell. Biol. 2004). The latter is based on tandem mass spectrometry, MS/MS or PSD experiments. In order to facilitate interpretation of complex spectra, peptides are chemically derivatized by appropriate reagents that, either almost exclusively or in most of the cases, give rise to one series of fragment ions. Mass difference between consecutive signals reveals amino acid sequence. Keough's idea of binding acidic group with N-terminus of peptide has proved successful. Such derivatized peptide bearing positive and negative charge at the same time can be depicted by the following formula: $^-O_3S-C_6H_5-A_1-A_2-A_3-A_4-A_5-X^+$, where A stands for any amino acid, and X for lysine or arginine (T. Keough et al. Proc. Natl. Acad. Sci. 1999, T. Keough et al. Rapid Commun. Mass Spectrom. 2000).

Current procedures of peptide or protein derivatization yield better results in comparison with complex analysis of non-derivatized peptides. This refers to derivatization of amino end of peptides with molecule analogues with one (Y. H Lee. et al. Proteomics 2004) or two or more sulfonyl groups (M. Cindrić & associates, Patent Application No. P20100044A, HR). Spectra obtained after peptide derivatization with reagent having ortho, para arrangement of sulfonyl groups (with respect to the reactive compound group) demonstrated sufficiently intense ion signals close to the site of derivatization, whereas distancing from the site of derivatization the signal would fade away or be lost. Ultimately, this method (M. Cindrić & associates, Patent Application No. P20100044A, HR) demonstrated very poor signal intensity for ions more distant from the site of derivatization and could not be used in the derivatization and detection of ions several amino acids away from the site of derivatization. (e.g. distance of 10 and more peptide bonds from the site of derivatization). Hence, the method of the foregoing application had a limited scope of successful amino acid sequence detection.

STATE OF THE ART

The most common sulfonyl group-containing reagents used in peptide or protein derivatization are 2-sulfobenzoic acid (T. Keough et al. Proc. Natl. Acad. Sci. 1999), sulfo-NHS esters (N-hydroxysuccinimide, NHS; W. R. Allery et al. J. Prot. Research 2007), and 4-sulfophenyl isothiocyanate (P. Chen et al. Rapid Commun. Mass Spectrom. 2004), which relatively quickly (up to 30 minutes) modify peptide and make it amenable to sequencing. Current literature describes sulpho-derivatization reagents based on the following reactive groups: isothiocyano (Y. H. Lee et al. Proteomics 2004), isocyano (P. Conrotto et al. J. Biomol. Techn. 2005), cyclic anhydride (T. Keough et al. Proc. Natl. Acad. Sci. 1999), and N-Hydroxysuccinimide (W. R. Allery et al. J. Prot Research 2007). Patent application P20100044A, HR describes peptide/protein derivatization by use of derivatization reagent 4-formylbenzene-1,3-disulphonic acid having two sulfonyl groups in ortho and para position. Derivatization by use of said compound produces signals whose intensity becomes lower as the distance among detected ions and the site of derivatization increases.

In the state of the art there are several patents/patent applications that reveal different methods of detection of amino acid sequence and/or identification of proteins, peptides. However, none of the below stated documents allows detection of intensive signals of ions in negative mode of operation of mass spectrometer which are distant from the site of derivatization.

The PCT/US00/00790 patent application describes a procedure based on the use of the compounds with one or more acidic groups with pKa lower than 2 for derivatization of peptide N-terminus. Furthermore, this invention implies that derivatized y-ions are used for analysis of fragments by mass spectrometry, which are devoid of a- and b-ions. Although derivatives of disulphonic acids are also mentioned as acidic groups, derivatization procedure described in this document is not used for spectra analysis in negative MS/MS mode Patent document PCT/US01/22815 refers to derivatization of lysine-containing peptides. As in the document mentioned above, derivatization procedure in this document is not used for spectra analysis in negative MS/MS mode. Furthermore, this document refers to guanidination, i.e., imidolization of lysine, which is not necessary with the use of the subject invention.

Patent application PCT/US02/16244 describes the use of water-stable reagents for peptide derivatization. The reagents comprise one or more sulfonyl groups bound with activated acidic group via aliphatic or aromatic linkage. Activated acid derivatives described in this patent application are acid esters, anhydrides of organic and inorganic acids. The activated acidic moiety particularly mentioned in this patent is NHS ester, allowing for all procedure steps to be carried out under aqueous conditions. The four basic steps in the subject invention include guanidination of lysine. Furthermore, this invention refers to the y-ions analysis in positive mode of operation of mass spectrometer. Derivatization procedure in this document is not used for spectra analysis in negative MS/MS mode.

Patent document PCT/US02/16247 holds priority of the application PCT/US02/16244, and, therefore, shares a high level of similarity with the latter patent. In comparison with the aforementioned patent, it has been added that polypeptides are immobilized on the solid support, at least in the step "a". This means that complete derivatization procedure is not carried out in solution, the latter being the case with subject invention. In addition, derivatization procedure in the aforementioned document is not used to analyse spectra in negative MS/MS mode.

European patent application EP 1561755 describes compounds with disulfide bond that react with peptide N-terminus followed by disulfide bond cleavage under oxidation or reduction conditions resulting in the formation of sulfonic acid derivatives. Functional group of disulfide compound that reacts with N-terminus was chosen among carboxyl group, isothiocyanate, succinimidyl oxycarbonyl groups, p-nitrophenoloxy carbonyl groups, pentafluorophenyloxy carbonyl groups, and tetrafluorosulpho phenyloxycarbonyl groups. Subject invention is used for detection of amino acid sequence by y-ions analysis in positive mode of operation of mass spectrometer. In this invention, guanidination of lysine is also necessary. In addition, derivatization procedure in the aforementioned document is not used for spectra analysis in negative MS/MS mode.

Patent application PCT/SE2005/000187 improves previous methods in such a way that removal of unmodified portions of peptides from the solution by ion exchange precedes the analysis of fragments in positive mode of operation of mass spectrometer. This procedure is used after any chemically-aided peptide derivatization.

Accordingly, conventional procedure of peptide derivatization in the state of the art was carried out by introduction of sulfonyl groups to N-terminus. N-terminus derivatized in this manner becomes negatively charged. Positively charged C-terminus is a counterbalance to negatively charged N-terminus resulting in the formation of the so called zwitterion, i.e., charge of derivatized protein or peptide equals zero. In further ionization procedure in mass spectrometer used in the state of the art, proton was added to peptide/protein reducing the energy necessary for peptide bonds cleavage, which produced mostly b- and y-ions. Since b-ions would be neutral due to negative charge at N-terminus, only positive y-ions in positive mode of operation of mass spectrometer were analysed in the state of the art.

Patent application WO 00/20870 describes a method of multiple cleavages using a variety of reagents. After polypeptide cleavage, the isolation process is described in detail. The method is designed to isolate particular peptides from the rest of the solution by attaching cleaved peptides to the solid phase through chromatography. The method does not improve the fragmentation process of peptides in mass spectrometer. Patent application WO 96/02003 describes use of newly synthesized alkoxy-thiocarbonyl-imidazole with smaller peptides cleavage. The newly synthesized reagent is an alkoxy thiourea derivative and binds to peptide N-terminus. The mechanism of its activity includes cleavage in the solution and use of acid, which cleaves off terminal amino acid in the form of thiazolinone derivative which cannot rearrange to a thiohydantoin. Thiazolinone can have fluorescent marking and analyzed by mass spectrometer. The method is adjusted to the operation in the solution and there are no data confirming improvement of fragmentation in mass spectrometer.

Patent application EP 1617224 describes ionization and fragmentation improvement in mass spectrometry by derivatization of peptide C-terminus by 2-methoxy-4,5-dihydro-1H-imidazole. Proposed derivatization and fragmentation mechanism by use of mass spectrometry has no similarity with sulfonyl derivatization reagents operation mechanism. The basicity of derivatized lysine (Lys-4,5-dihydro-1H-imidazole fragment) is in direct correlation with ion intensity in mass spectrometer. Secondary amines bound to lysine by derivatization with 2-methoxy-4,5-dihydro-1H-imidazole are one of the strongest non-ionic bases, i.e., the mechanism of their activity is connected with strong proton binding with peptide. Completely opposed to said mechanism is the mechanism of activity of sulfonyl groups. Sulfonyl groups release protons and in this manner they increase peptide acidity and facilitate fragmentation in mass spectrometer.

Patent application P20100044A, HR describes a process of using 4-formyl-benzene-1,3-disulphonic acid (two sulfonyl groups in ortho and para position with respect to the aldehyde reactive group) for detection of amino acid sequences. The arrangement of sulfonyl groups situated in ortho and para position in benzene hinders donating of labile proton to distant amino acid amides, reducing the possibility of detection of amino acids distant from the site of derivatization. Consequently, incomplete amino acid sequence and/or protein or peptide detection results are obtained.

DISCLOSURE OF THE INVENTION

Based on the knowledge comprised in the state of the art that refers to methods of detection of amino acid sequence and/or identification of proteins, peptides, in particular the patent application HR P20100044A, it has become clear that the methods known so far could not give good results of protein or peptide detection wherein it was necessary to detect signals of ions that are distant from the site of derivatization. As the main objective of derivatization reagent activity is to achieve a series of most intensive signals and, thus, determine unambiguously the amino acid sequence of the entire peptide, the compound of general formula I, i.e., two sulfonyl groups in optimum position (meta, meta) in said compound enable the determination of intensive signals which could not be revealed with different sulfonyl group arrangement (e.g. ortho, para). Determination of the entire sequence of peptide or of its major portion increases unambiguousness of the result obtained and facilitates identification of proteins with increased correctness and accuracy of measurement.

Considering that derivatization reagents containing two or more sulfonyl groups which were commercially available did not provide good results, non-commercially available compounds which are not usually applied or are rarely applied in various researches were synthesized.

Compounds of general formula I were obtained by different synthesis procedures

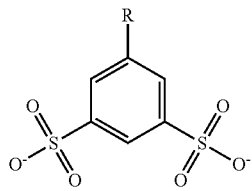

(I)

where R is a reactive group selected from aldehyde-, keto-, isothiocyanate-, isocyanate-group, NHS ester, anhydride or activated carboxylic acid group.

In the foregoing compounds group, sulfonyl groups are in meta, meta position with respect to the reactive compound group. Upon examination of derivatization compounds of general formula I in the method of detection of amino acid sequence and/or identification of proteins, peptides in negative mode of operation, it was unexpectedly established that such synthesized compounds of general formula I allow for more precise (detailed) detection of amino acid sequence and/or identification of proteins, peptides in comparison with the compounds in negative mode of operation used so far.

Namely, by applying obtained compounds of general formula I in the derivatization procedure, it was established that by use of compound of general formula I as derivatization reagent in negative mode of operation of mass spectrometer, the signal intensity of ions distant from the site of derivatization is unexpectedly multiply increased in comparison with the earlier use of 4-formyl-benzene-1,3-disulphonic acid or another compound containing two sulfonyl groups in ortho and para position with respect to the reactive group. Ions distance from the site of derivatization where such unexpected effect of the compound of general formula I is noticeable depends on detected protein, peptide or amino acid sequence. Current results have shown that the unexpected effects of this invention generally appear at the distance at which ion intensity commences decreasing with the use of compound containing two sulfonyl groups in ortho and para position with respect to the reactive group. That value dependent upon amino acid sequence appears in ions of amino acids distant from the site of derivatization (distance from the site of derivatization where increase in ion intensity commences to be noticeable can vary from 5 to 10 amino acids).

Use of the compound of general formula I in the method of detection of amino acid sequence in negative mode of operation enables unambiguous analysis of the signal of ions in negative mode of operation of mass spectrometer which are distant from the site of derivatization. Considering that use of derivatization compounds used so far in negative mode of operation enabled no analysis of the signals of ions distant from the site of derivatization, change of the compounds of subject invention in the foregoing method provides more detailed and accurate results in comparison with derivatization compounds used so far in said detection method.

Therefore, subject invention reveals an improved method of detection of amino acid sequence of peptides/proteins, i.e., method of identification of peptides/proteins comprising the following steps:

derivatization of peptides and/or proteins at N-terminus by compound of general formula I comprising R reactive group that binds with amino group of N-terminus;

analysis of one or more derivatized analytes by acquisition of spectra of derivatized negative ions in negative mode of operation of mass spectrometers;

interpretation of obtained fragmentation pattern as to detect amino acid sequence, i.e., to identify the aforementioned analyte.

The subject step of derivatization of peptides and/or proteins gives rise to exclusively one series of fragmented ions. Precisely, this step produces singly charged derivatized negative ions. During derivatization in the subject invention with the compound comprising two sulfonyl groups, one sulfonyl group neutralizes positive ion charge, whereas the other sulfonyl group gives negative charge to derivatized ion. If the sulfonyl groups are situated at equidistant meta, meta distance from the site of derivatization, proton donation necessary for cleavage of amide bonds and production of signals is more pronounced. This new and unexpected effect allows detection of obtained derivatized negative ions in negative mode of operation of mass spectrometer, especially if ions are several amide bonds away from the site of derivatization in comparison with any known means of derivatization.

Unlike the aforementioned invention, current procedures of peptide or protein derivatization did yield better results in comparison with complex analysis of non-derivatized peptides. This refers to derivatization of amino end of peptides with molecule analogues with one (Y. H Lee. et al. Proteomics 2004) or two or more sulfonyl groups (M. Cindrić & associates, Patent Application No. P20100044A, HR). However, spectra obtained after peptide derivatization with reagent having ortho, para arrangement of sulfonyl groups demonstrated limitations in the analysis of distant amino acids. Since ortho group is in direct proximity of the site of derivatization the majority of protons donated by ortho-sulfonyl group in mass spectrometer is consumed for cleaving off active benzo-disulfonyl group of reagents (intensive signal visible in negative MS/MS spectrum at m/z 249). Cleaving off active benzo-disulfonyl group reduces further reagent activity in mass spectrometer, which manifests by reduction of mobile proton range. Distancing the sulfonyl group from the site of derivatization and placing sulfonyl groups into equidistant position as in the case of meta, meta arrangement of sulfonyl groups prevents completely derivatization reagent to be cleaved off during analysis, increasing thereby mobile proton range and intensity of the signal of cleaved off peptide bonds which are distant from the site of derivatization (signal in negative MS/MS spectrum at m/z 249 is absent). The range of mobile proton is connected with the nature of analyzed peptides, but in the direct comparison between ortho, para sulfonyl groups and meta, meta sulfonyl groups, meta, meta arrangement has always resulted in broader mobile proton range and, thus, also in more intensive signals in total starting from the site of derivatization to C-terminus.

Therefore, unlike peptide derivatization by compounds comprising two sulfonyl groups with no equidistant meta, meta distance among sulfonyl groups and the reactive group (patent application P20100044A, HR), in the compounds of general formula I, where sulfonyl groups are in meta, meta position with respect to the reactive group, interference of adjacent molecular groups is reduced and easier proton donation is allowed. The advantage of the subject method is that the signal detected in MS/MS scan of derivatized negative ions predominates over the signals of positive y ions obtained by derivatization by the compounds comprising one sulfonyl group for at least 5-fold in an absolute amount measured for an equal amount of analyte applied onto MALDI plate. Furthermore, the advantage of the subject method over the analysis of peptide ions comprising two sulfonyl groups which are not equidistant with respect to the reactive group in the molecule is an increased proton range in negative mode of operation measured for an equal amount of analyte applied onto MALDI plate.

Finally, use of the compound of general formula I increases reactive group reactivity, as meta, meta sulfonyl groups are two chemical bonds away from the site of aldehyde binding with amine whereby mobile proton range is improved, facilitating peptide analysis with increase of signal intensity of amino acid ions distant from the site of derivatization.

Furthermore, upon synthesizing of the compounds of general formula I, a so far unknown synthesis procedure of 5-formylbenzene-1,3-disulphonic acid was developed. The new synthesis procedure of 5-formylbenzene-1,3-disulphonic acid comprises the following steps:

Conversion of 3,5-dihydroxybenzaldehyde into O-benzaldehyde-3,5-bis(N,N-dimethylthiocarbamate) by use of relevant N,N-dialkylcarbamoylchloride with organic or inorganic bases in suitable organic solvent;

Rearrangement of O-benzaldehyde-3,5-bis(N,N-dimethylthiocarbamate) to obtain S-benzaldehyde-3,5-bis(N,N-dimethylthiocarbamate); rearrangement reaction can be performed thermally without solvent or with relevant high-boiling solvent at 150-280° C. or catalytically by use of palladium complex or Lewis acid);

Conversion of S-benzaldehyde-3,5-bis(N,N-dimethylthiocarbamate) into S-benzylalcohol-3,5-bis(N,N-dimethylthiocarbamate) by catalytic hydrogenation or reduction with complex metal hydrides, and then into S-benzylacetate-3,5-bis(N,N-dimethylthiocarbamate) by use of acetic acid chloride or anhydride;

Oxidation of S-benzylacetate-3,5-bis(N,N-dimethylthiocarbamate) into benzylalcohol-3,5-disulphonic acid with suitable organic or inorganic oxidant;

Oxidation of benzylalcohol-3,5-disulphonic acid into 5-formylbenzyl-1,3-disulphonic acid by use of pyridinium chlorochromate.

The reaction scheme of the new synthesis procedure of 5-formyl-benzene-1,3-disulphonic acid is as follows:

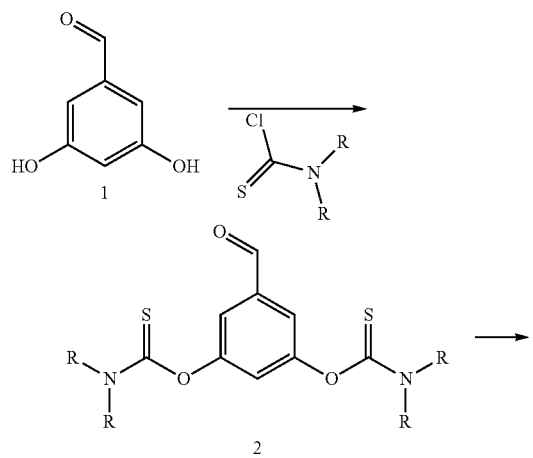

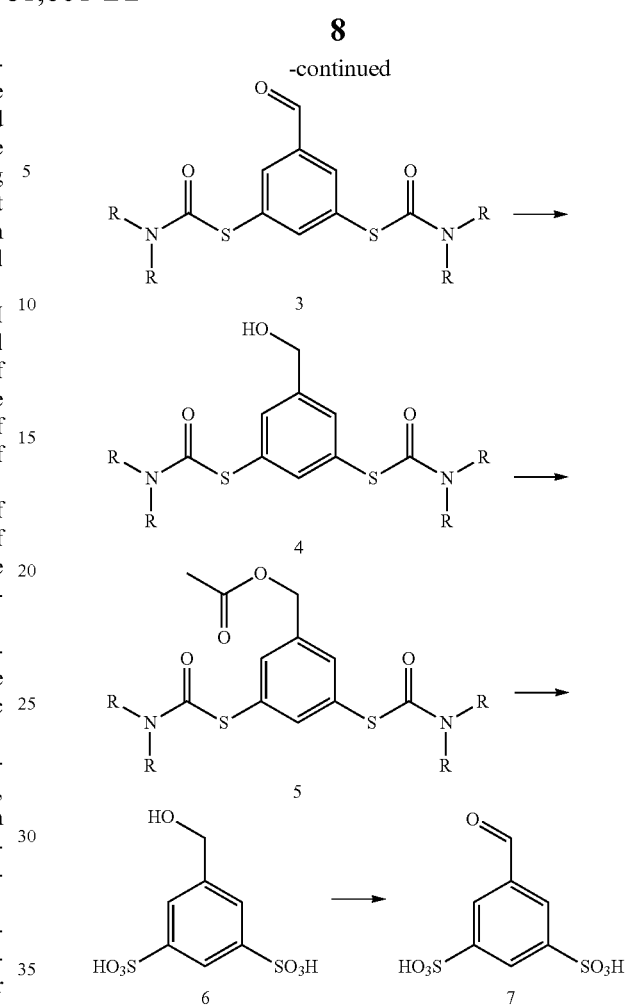

In said synthesis the reactions of oxidation and reduction have been performed on the target substituent successfully, despite both functional groups being susceptible to both oxidations and reductions. Introduction of additional reactions: aldehyde reduction, acetyl protection, deprotection and again oxidation enabled to carry out targeted desired reactions of oxidation and reduction and to obtain as a result compound 5-formyl-benzene-1,3-disulphonic acid.

The term "derivatization compound" in the subject invention refers to the compound of general formula I.

The term "reactive group" in the subject invention refers to any functional group known to the person skilled in the relevant art to react with amino group.

The term "analyte" in the subject invention refers to any portion (segment) of peptide and/or protein produced in the derivatization step, analysed in mass spectrometer.

DETAILED DESCRIPTION OF THE INVENTION

Analysis of Peptides/Proteins Using the Compound of General Formula I

The method presented by the subject invention enables detection of complete amino acid sequence of proteins, i.e., peptides. In protein identification, protein cleavage with known chemical or enzymatic proteolytic procedures precedes the method of the subject invention. Thus, proteins can be cleaved for example with chemical compounds such as ninhydrin, cyanogen bromide or by simple degradation using acid hydrolysis. Furthermore, proteins can be cleaved with enzymes such as trypsin, chymotrypsin, thermolysin, Lys-C, Glu-C, Arg-C, etc.

Figure 2:
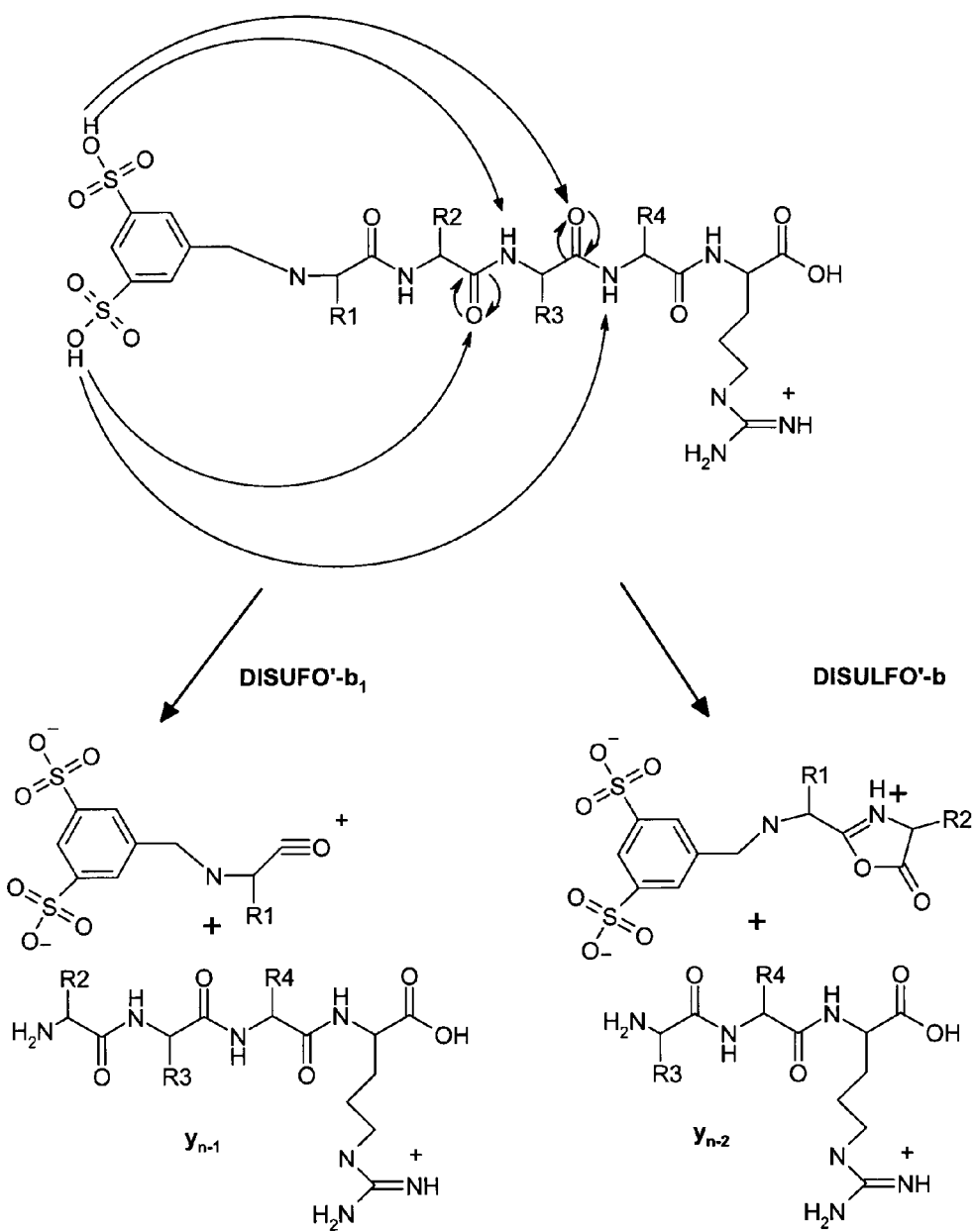
FIG. 2 represents cleavage mechanism of analytes in mass spectrometer.

The procedure of protein proteolysis, involving in the majority of cases peptides up to 5000 Da, with the possibility of derivatization of larger peptides as well, is followed by peptide mass determination by mass spectrometry and thereafter peptide derivatization procedure. Derivatization compound of general formula I is added to aqueous solution of peptides/proteins to be derivatized. Derivatization compound binds to N-terminus of peptide via reactive group giving it two sulfonyl groups and increasing its mass. Therefore, during the mass spectrometry, it is necessary to add thereto the m/z value of the relevant derivatization compound comprising two sulfonyl groups to the peptide mass (in MS/MS positive mode of operation the reagent is detached during analyses yielding products; y-ions that can reveal amino acid sequence, whereas in MS/MS negative mode of operation the reagent is not detached from N-terminus, but the formation of products; derivatized b-ions revealing amino acid sequence is still increased). Therefore, N-terminus is doubly negatively charged, whereas C-terminus or some basic side branch of peptide and/or protein is positively charged. When sulfonyl groups donate labile protons to amide groups, peptide and/or protein dissociates into amino acid integral portions. Resulting positive ions do not differ in mass from the positive ions of non-derivatized analogue, since sulfonyl groups during proton donation to amide bond in the peptide cleave off either a portion of ions from N-terminus of peptide chain or derivatization compound itself, thus producing gradually shorter peptide/protein ions. The same mechanisms in negative mode of operation yields the final reaction products, i.e., negatively charged derivatized ions comprising two sulfonyl groups at N-terminus, which increase the mass of precursor ions and product ions for the mass values of derivatization reagent (FIG. 2). However, regardless of the addition of derivatization group, the differences between detected ions in positive or negative mode of operation of mass spectrometry are equal, which ultimately enables determination of amino acid sequence or their modifications. The arrangement of sulfonyl groups with respect to the site where aldehyde of derivatization compound binds with peptide amine is equidistant (meta, meta), i.e., both groups are equally distant from the binding site, but they are not in direct proximity of reactive group. Such arrangement of sulfonyl groups with respect to the other disulfonyl analogues allows easier proton donation to amide groups on the peptide.

Derivatized negative ions can be analysed in different mass spectrometers. Thus, the following mass spectrometers are used: time-of-flight (TOF), tandem mass analyzers (MS/MS, QQQ, MS/Q, Q/TOF), quadropole (Q), ion trap (IT) and similar devices. Moreover, experiments have shown that the use of MALDI ion source in the subject invention gives rise to exclusively y fragments of positive ions and derivatized negative b-ions. Signals obtained by analysis of these derivatized negative b-ions produced in the subject procedure are extremely intensive, whereas noise in comparison with standard methods of detection of amino acid sequence or identification of peptide/protein is up to 10-fold lower. Thus, the overall increase of signal intensity obtained by the subject invention is up to 15-fold higher than the signal intensities obtained by the methods in the state of the art, except in the case of derivatization by other derivatization compounds where sulfonyl groups are in ortho, para position with respect to the reactive group.

Figures 3A, 3B:
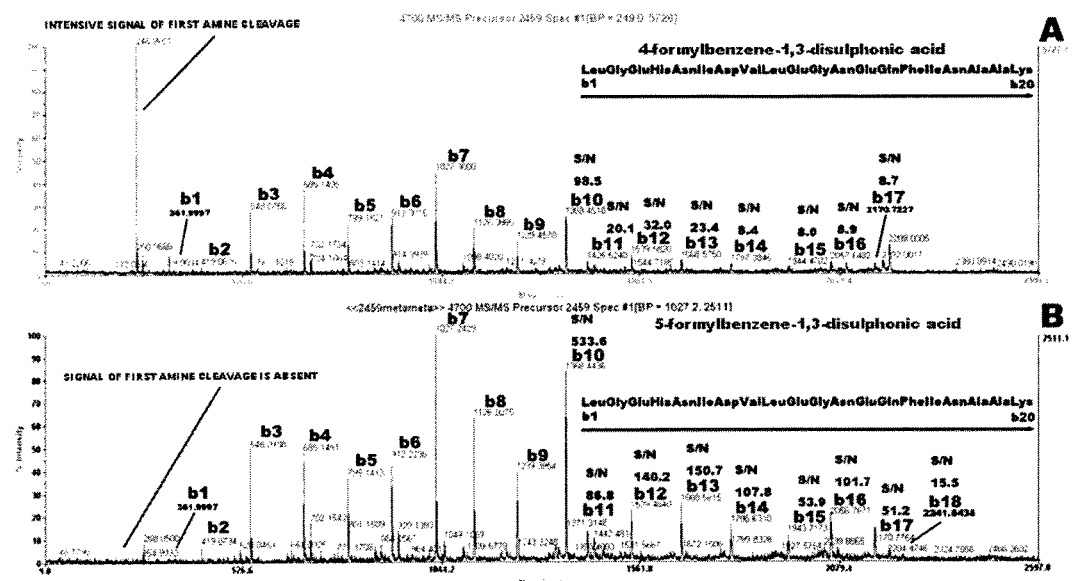
FIG. 3 represents MS/MS mass spectra for equal amounts of analyzed analytes of tryptic digests of trypsin autolysis (1 ng) of: (3A) LeuGlyGluHisAsnIleAspValLeuGluGlyAsnGluGlnPheIleAsnAlaAlaLys peptide SEQ ID NO: 1) derivatized by derivatization compound 4-formyl-benzene-1,3- disulphonic acid with two sulfonyl groups in ortho and para position acquired in the negative mode of operation of mass spectrometer and (3B) LeuGlyGluHisAsnIleAspValLeuGluGlyAsnGluGlnPheIleAsnAlaAlaLys peptide SEQ ID NO: 1) derivatized with derivatization compound 5-formyl-benzene-1,3-disulphonic acid with two sulfonyl groups in meta and meta position acquired in negative mode of operation of mass spectrometer.

In the particular example compared results are obtained by derivatization with the use of 4-formyl-benzene-1,3-disulphonic acid (compound of patent application P20100044A) and 5-formyl-benzene-1,3-disulphonic acid. In comparison with derivatization with the use of 4-formyl-benzene-1,3-disulphonic acid the improvement of signal intensity by amino acids which are 10 and more amino acids away from the site of derivatization is up to 10-fold higher with respect to the noise after peptide derivatization with 5-formyl-benzene-1,3-disulphonic acid (FIG. 3A and FIG. 3B and Table 1). Improvement of mobile proton range is allowed by different arrangement of sulfonyl groups (meta, meta in 5-formyl-benzene-1,3-disulphonic acid with respect to ortho, para in 4-formyl-benzene-1,3-disulphonic acid). Ortho sulfonyl group donates the majority of its protons to the nearest amine produced after derivatization of N-terminus, which is visible in spectra of peptide cleavage in negative mode of operation of mass spectrometer where measured signal at m/z 249 is often the most intensive in the spectrum (signal produced after reagent cleavage at the site of derivatization). Such pronounced derivatization reagent cleaving off is absent when sulfonyl groups are in meta, meta position. Moreover, meta, meta sulfonyl groups do not hinder derivatization of N-terminus as noticed when sulfonyl groups are in direct proximity of benzaldehyde group (ortho position). Due to said reasons ortho sulfonyl group hinders derivatization and uses the majority of its protons to cleave off the nearest nitrogen reducing the activity range of mobile proton towards distant amino acids. The comparison was carried out under the same conditions in mass spectrometer and with the same amount of derivatization peptides (1 ng of tryptic digest of trypsin autolysis). However, by using mass spectrometers that cleave peptides/proteins in a different manner, it is possible to obtain with the subject invention also other fragments of negative and positive ions, maintaining the basic component of amino acid sequence determination based on the difference between masses of signal sequence.

Direct comparison of the compound used in the state of the art (4-formylbenzene-1,3-disulphonic acid) and the newly synthesized compound (5-formylbenzene-1,3-disulphonic acid) reveals increase of signal intensity of b-ions of amino acids, and extended range of derivatization reagent. This increase is most contributed by meta, meta arrangement of sulfonyl groups which do not sterically hinder the derivatization procedure, and do not enter into interaction in mass spectrometer with the nearest amino or amide protons.

TABLE 1

Comparison of signal intensity of peptide b-ions 10 or more amino acids away from the site of derivatization of LeuGlyGluHisAsnIleAspValLeuGluGlyAsnGluGlnPheIleAsnAlaAlaLys peptide (SEQ ID NO: 1) after derivatization with 4-formyl-benzene-1,3-disulphonic acid (ortho, para) and with 5-formyl-benzene-1,3-disulphonic acid (meta, meta). Signals of b-ions less than 10 amino acids away were not taken into calculation considering that in that field calculated S/N is the same for both derivatization reagents.

| Fragment m/z | Amino acid | Distance from the site of derivatization | Measured signal-to-noise ratio (S/N) (ortho, para)/(meta, meta) |
|---|---|---|---|
| 1368 | Glu | 10 | 98, 5/533, 6 |
| 1425 | Gly | 11 | 20, 1/86, 8 |
| 1539 | Asn | 12 | 32, 0/140, 2 |
| 1668 | Glu | 13 | 23, 4/150, 7 |
| 1796 | Gln | 14 | 8, 4/107, 8 |
| 1943 | Phe | 15 | 8, 0/53, 9 |
| 2056 | Ile | 16 | 8, 9/101, 7 |
| 2170 | Asn | 17 | 8, 7/51, 2 |
| 2241 | Ala | 18 | 0, 0/15, 5 |

Reactive group of derivatization compound can be any group reacting with amino group. It is preferable that reactive group of the compound used in derivatization step of the subject invention is selected from the group comprising aldehyde, keto-, isothiocyanate-, isocyanate-group, NHS ester, anhydride or activated carboxylic acid group.

It is most preferred that, in the subject invention, reactive group of derivatization compound is aldehyde group. In the cases where in the subject invention compound with aldehyde reactive group at ph 1-5 is used, aldehyde group selectively reacts with N-terminus of peptide or protein, without binding to other amino groups in protein or peptide chain. By using this approach dual derivatization of tryptic peptides is avoided, since derivatization reaction performed according to the subject invention selectively derivatized N-terminus without the need of adding protective group at lysine. Since in this case lysine guanidination is redundant, the method of detection of amino acid sequence, i.e., peptide/protein identification is additionally simplified. Also, since guanidination, which causes significant quantitative losses during sample handling, is not needed, signal intensity in the analysis of derivatizated negative ions in negative mode of operation of mass spectrometry is increased. It is most preferred that compound with aldehyde group in derivatization step is used at approximately pH 4. Furthermore, it is preferable that during the use of derivatization compound with aldehyde reactive group, NaCNBH4 is also added to aqueous solution as to reduce imino-group of the resulting Schiff base.

Moreover, it is most preferred to use 5-formyl-benzene-1,3-disulphonic acid as compound in derivatization step.

One of the Embodiments of the Invention

Example 1

Use of 5-formylbenzene-1,3-disulphonic acid as a Derivatization Compound

In this example the method of peptide derivatization of the subject invention by chemical reaction in two stages was used: first stage includes condensation of aldehyde and primary amine with production of Schiff base, and the second stage includes reduction of imines of Schiff base into amines. The reagents used included: 5-formyl-benzene-1,3-disulphonic acid (synthesized at "Rudjer Boskovic" Institute), NaCNBH4 (Merck, Darmstadt, Germany), and peptides obtained by trypsin autolysis (Merck, Darmstadt, Germany), CHCA matrix (α-cyano-4-hydroxycinnamic acid, Sigma Aldrich, St. Louis, Wis., USA).

Table 2 presents trypsin peptide and its ion detected by mass spectrometry, which are produced during trypsin autolysis prior to derivatization by 5-formyl-benzene-1,3-disulphonic acid.

TABLE 2

Peptide produced by trypsin autolysis with theoretical calculation of masses of corresponding ions.

| FRAGMENT | m + H | sequence (SEQ ID NO: 1) |
|---|---|---|
| T3 | 2211.1000 | LeuGlyGluHisAsnIleAspValLeuGlu GlyAsnGluGlnPheIleAsnAlaAlaLys |

Upon purification of 1 μg fragments derived from trypsin autolysis using ZipTip technique, peptide mixture was evaporated using SpeedVac (Eppendorf, Germany) concentrator followed by addition of 1 mg 5-formyl-benzene-1,3-disulphonic acid and 4 mg NaCNBH₄ dissolved in 100 μl phosphate buffer pH 4.0 to dried concentrate. The solution was stored in the fridge at temperature of 4-8° C. for 12 hours to react. Subsequently, 10 μl of the solution was purified again using ZipTip, dried in SpeedVac concentrator and dissolved in 5 μl CHCA matrix with 5 mg/ml concentration. 1 μl of this solution was applied onto MALDI metal plate and analysed by mass spectrometer.

Derivatization procedure of peptides (SEQ ID NO: 1) obtained by protein cleavage by trypsin at N-terminus is illustrated by the following reaction:

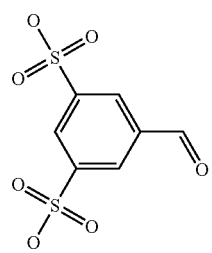

5-FORMYLBENZENE-1,3-DISULPHONIC ACID

-continued

T3 trypsin autolysis fragment

NH$_2$—LeuGly Glu His Asn Ile AspVal LeuGlu Gly AsnGlu Gln Phe Ile AsnAla Ala Lys—COOH

NaCNBH4
pH 1-5

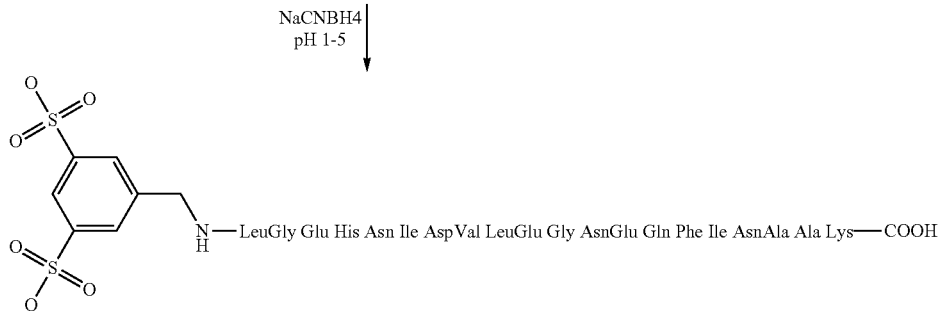

The example of instrumental MS/MS fragmentation of analytes originally derived from trypsin autolysis shows significant improvement of structural analysis of produced analytes, which increases accuracy of amino acid sequence detection (so called de novo sequencing of unknown peptides).

For the purpose of evaluation of method success, MS/MS spectra were acquired on MALDI-TOF/TOF instrument before and after derivatization. An example presented in FIG. 3 gives a comparison of MS/MS spectra of negative b-ions of ion derivatized by 4-formylbenzene-1,3-disulphonic acid of lysine fragment LeuGlyGluHisAsnIleAspValLeuGluGlyAsnGluGlnPheIleAsnAlaAlaLys (SEQ ID NO: 1) (FIG. 3A) and MS/MS spectra of negative b-ions after derivatization by 5-formyl-benzene-1,3-disulphonic acid (FIG. 3B). It is important to point out that MS/MS spectra of negative derivatized ions are acquired on the same sample, i.e., on the same ions obtained after derivatization, and that the amount of used analyte was the same as the conditions of acquisition of both derivatized peptides.

Produced negative b ions differ in mass for m/z 247,945 in comparison with underivatized fragments. During MS/MS analysis of negatively charged ions of derivatized fragment, it is possible to detect only b ions that kept sulfonyl groups, which requires that an increment of m/z 247,945 is added (FIGS. 2A and 2B). Extremely intensive signal produced by cleaving off derivatization reagent m/z 249 (247,945+1H$^+$) is absent in the case of use of 5-formyl-benzene-1,3-disulphonic acid which proved higher mobile proton affinity for distant amino acids (FIG. 3B). Extremely intensive signal m/z 249 indicates consumption of large portion of protons situated in ortho position in sulfonyl group on cleavage of the nearest amino group (site of derivatization, i.e., derivatization reagent).

Comparison of spectra in FIGS. 3A and 3B shows significant increase in measured ion signals in spectrum in FIG. 3B in comparison with equivalent signals in FIG. 3A (signals ten and more amide bonds away from the site of derivatization), which proves that the subject method increases success in detection of amino acid sequence of peptides.

If up to 10-fold lower noise detected in analysis of derivatized ions with 5-formylbenzene-1,3-disulphonic acid is added, the overall increase in signal-to-noise ratio (S/N) after derivatization is 15-fold for MS/MS negative ions. If ions of amino acids presented in FIGS. 3A and 3B are compared, significant difference is noticeable after the tenth signal in amino acid sequence (m/z 1368) in favour of signal increase of peptide ions derivatized with 5-formyl-benzene-1,3-disulphonic acid (Table 1 and FIG. 3B). Similar experiments were carried out on all ions consisting of 10 or more amino acids presented in Table 1 before and after derivatization, and obtained results do not differ from the results set out in this example.

Method described in the subject patent application is technically rapid, cost effective and reliable, and could be of high value in proteomics analyses of various samples, especially the biological ones. In fact, only in humans the size of the whole proteome is estimated to several million protein species, and databases currently provide information on completely determined amino acid sequences for approximately 1.5 million proteins. The described method could, thus, facilitate simple determination of amino acid sequences of human proteins unidentified so far with significant medical implications (e.g. biomarker discovery). It would also be as simple to identify proteins for different biological species for which publicly accessible protein databases, such as NCBI and UNIPROT, contain no exact information on amino acid sequences.

Subject method reduces the time of sub-structural analyses of proteins and peptides by mass spectrometry (MS/MS analysis) and increases accuracy when searching protein databases.

Detailed Description of
5-formyl-benzene-1,3-disulphonic acid Synthesis

Figure 1:
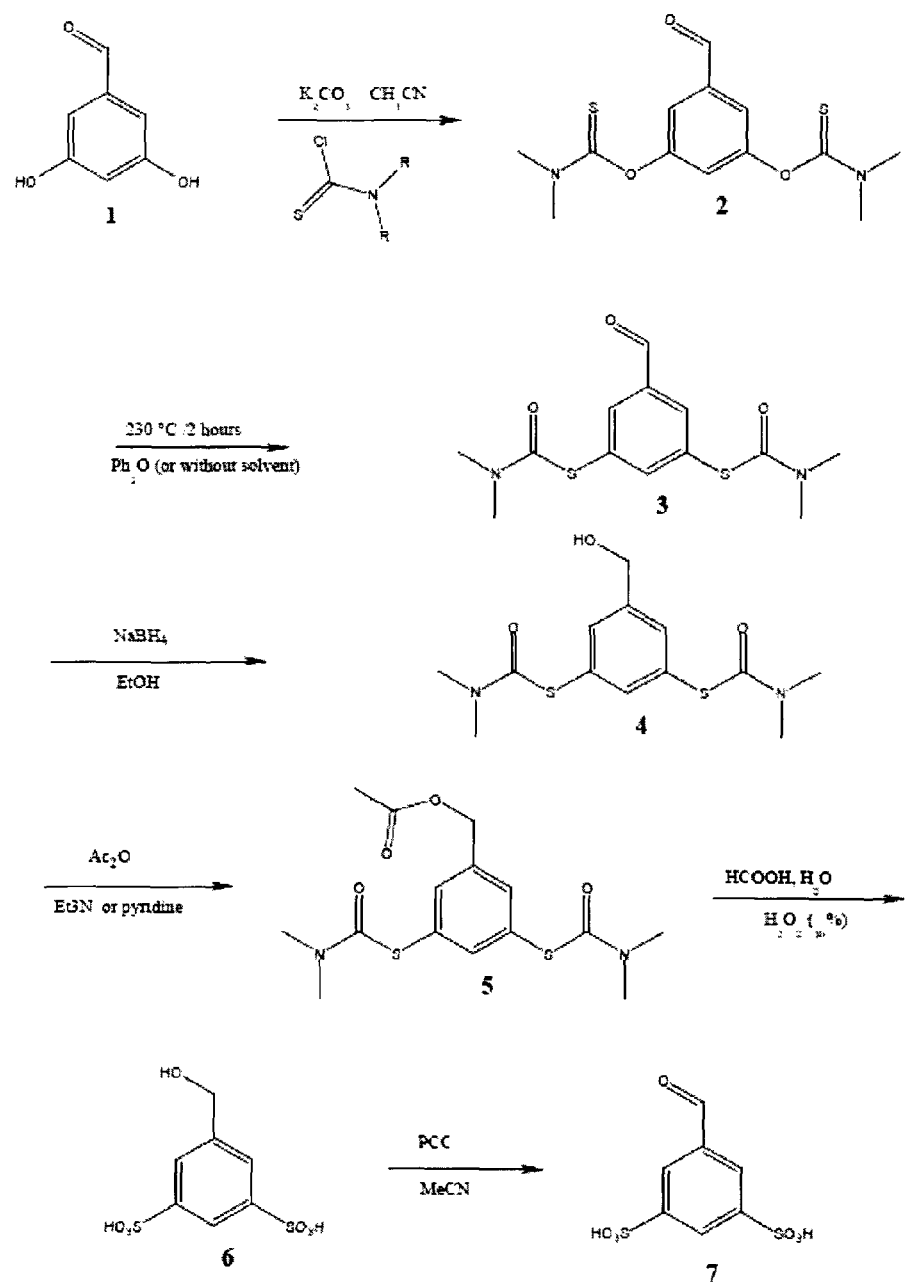
FIG. 1 represents the route of synthesis of 5-formyl-benzene-1,3-disulphonic acid (synthesis is described in "Detailed description of the invention")

The numbers of synthesized intermediates and final product correspond to the numbers in FIG. 1.

1. O-benzaldehyde-3,
5-bis(N,N-dimethylthiocarbamate) (2)

To the solution of 3,5-dihydroxybenzaldehyde (630 mg, 4.5 mmol, Sigma-Aldrich, St. Louis, Wis., USA) 3.0 g (22 mmol) K$_2$CO$_3$ (Kemika, Zagreb, Croatia) and 1.25 g (10 mmol) N,N-dimethylcarbamoylchloride (Sigma-Aldrich, St. Louis, Wis., USA) were added in 50 ml dry acetonitrile. Reaction mixture was mixed for 24 hours at room temperature, 20 ml water and 0.5 g KOH were added and mixed another 30 minutes. The majority of acetonitrile was evaporated and water solution extracted with use of dichlormethane (30+20 ml). Organic extracts were washed with saturated NaCl solution, dried and evaporated. Pre-crystallization from methanol produced 980 mg (70%) of pure product.

1H NMR (CDCl$_3$): 3.37 (s, 6H); 3.46 (s, 6H); 7.14 (t, J=2.3 Hz, 1H); 7.49 (d, J=2.3 Hz, 2H); 9.98 (s, 1H) ppm.

13C NMR (CDCl$_3$): 38.90; 43.39; 121.33; 124.30; 137.53; 154.55; 186.77; 190.08.

2. S-benzaldehyde-3,5-bis(N,N-dimethylthiocarbamate) (3)

Carbamate 2 (350 mg, mmol) was heated in 2 ml diphenyl ether (Sigma-Aldrich, St. Louis, Wis., USA) at 230° C. for 2 hours. With use of chromatography on silica gel column (Sigma-Aldrich, St. Louis, Wis., USA) in addition to hexane-dichlormethane-ethylacetate, 315 mg (90%) of pure product was obtained.

1H NMR (CDCl$_3$): 3.04 (brs, 6H); 3.08 (brs, 12H); 7.88 (t, J=1.6 Hz, 1H); 8.00 (d, J=1.6 Hz, 2H); 9.99 (s, 1H) ppm.

13C NMR (CDCl$_3$): 37.08; 131.16; 136.97; 137.25; 147.39; 165.53; 190.55 ppm.

3. S-benzylalcohol-3,5-bis(N,N-dimethylthiocarbamate) (4)

Thylthiocarbamate 3 (315 mg) was dissolved in 40 ml ethanol and 50 mg NaBH$_4$ (Sigma-Aldrich, Buchs, Switzerland) was added. The solution was mixed for 1 hour at room temperature, hydride residue was destroyed with ammonium chloride solution (Kemika, Zagreb, Croatia), ethanol was evaporated, and the product extracted with use of dichloromethane. Pure product in the amount of 320 mg (100%) was obtained.

4. S-benzylacetate-3,5-bis(N,N-dimethylthiocarbamate) (5)

To the solution of compound 4 (320 mg) 1.0 ml triethylamine (Sigma-Aldrich, St. Louis, Wis., USA) and 0.9 ml acetic acid anhydride (Kemika, Zagreb, Croatia) were added in 30 ml dichloromethane. After 3 hours anhydride residue was destroyed with addition of methanol. Reaction solution was washed with 2% HCl solution, dried and evaporated. Acetate 5 in the amount of 330 mg (91%) was obtained.

1H NMR (CDCl$_3$): 2.09 (s, 3H); 3.05 (brs, 12H); 7.51 (d, J=1.2 Hz, 2H); 7.60 (t, J=1.2 Hz, 1H) ppm.

13C NMR (CDCl$_3$): 20.97; 36.98; 65.26; 129.77; 135.83; 137.15; 141.87; 166.15; 170.69 ppm.

5. Benzylalcohol-3,5-disulphonic acid (6)

To the cooled mixture of formic acid (15 g, Kemika, Zagreb, Croatia), water (1.8 g) and hydrogen peroxide (30%, 1.5 g, Kemika, Zagreb, Croatia) 125 mg acetate 5 was added. Reaction mixture was mixed for 20 hours at room temperature and evaporated to dryness. The raw product was passed through a column of Amberlite IR-120 (H$^+$), (Rohm and Haas, Philadelphia, Pa., USA); the water solution was evaporated to dryness, and the residue was dissolved in 20 ml methanol and heated to boiling point for 30 minutes. Evaporation of the solution produced 90 mg (95%) of product 6.

1H NMR (CD$_3$OD): 4.68 (s, 2H); 7.91 (s, 2H); 8.21 (s, 1H) ppm.

13C NMR (CD$_3$OD): 62.94; 122.09; 125.53; 142.91; 145.08 ppm.

No alternative oxidation route was found in the literature, and there is the possibility that other peroxyacids in aqueous acid conditions are able to oxidize the resulting compound in the same manner.

6. Benzaldehyde-3,5-disulphonic acid (7)

Alcohol 6 (100 mg, 0.37 mmol) was dissolved in 30 ml dry acetonitrile. Pyridinium chlorochromate (Prepared according to: E. J. Corey and W. Suggs, Tetrahedron Lett. 1975, 16, 2647-2650) in the amount of 90 mg (0.41 mmol) was added to the solution and mixed for 2 hours at room temperature. The solvent was evaporated and 50 ml methanol and 3 ml ammonia (25%) were added. After 3 hours the residue was filtered, the solvent was evaporated, and the remaining was passed through a column of Amberlite IR-120 (H$^+$). Disulphonic acid 7 in the amount of 80 mg (80%) was obtained.

There are many other, more or less alternative reagents for which authors claim that they oxidise alcohol into aldehyde.

1H NMR (D$_2$O): 8.36 (s, 3H); 9.96 (s, 1H) ppm.

13C NMR (D$_2$O): 126.65; 128.25; 129.05; 137.07; 193.86 ppm.

Shown examples of the methods of derivatization and synthesis of 5-formyl-benzene-1,3-disulphonic acid present only some of the embodiments of the subject invention and have no limitation on the scope of patent protection of the subject invention.

The invention claimed is:

1. A method of detection of amino acid sequence and identification of peptides and/or proteins, comprising the following steps:
   selective derivatization of peptides and/or proteins at N-terminus having unprotected epsilon-amine of lysine, wherein the selective derivatization is carried out at pH 1-5 with addition of sodium cyanoborohydride (NaBH$_4$CN) using 5-formylbenzene-1,3-disulphonic acid, wherein the selective derivatization comprises reacting of the aldehyde group with an amino group at the N-terminus of the peptide or protein to form derivatized analytes in a form of a secondary amine;
   analysis of one or more of the derivatized analytes by acquisition of spectra of derivatized negative ions acquired in the MS/MS negative mode of operation of a mass spectrometer; and
   interpretation of an obtained fragmentation pattern to detect amino acid sequence and to identify the aforementioned analyte.

2. The method according to claim 1, wherein in the analysis step, the spectra of derivatized negative b-ions is acquired in the MS/MS negative mode of operation of the mass spectrometer.

* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Sus scrofa

<400> SEQUENCE: 1

Leu Gly Glu His Asn Ile Asp Val Leu Glu Gly Asn Glu Gln Phe Ile
1               5                   10                  15

Asn Ala Ala Lys
            20
```